US006285897B1

(12) United States Patent
Kilcoyne et al.

(10) Patent No.: US 6,285,897 B1
(45) Date of Patent: Sep. 4, 2001

(54) REMOTE PHYSIOLOGICAL MONITORING SYSTEM

(75) Inventors: John T. Kilcoyne; Ross Tsukashima, both of San Diego; George M. Johnson, Santa Ana; Christopher Klecher, San Diego, all of CA (US)

(73) Assignee: Endonetics, Inc., San Diego, CA (US)

( * ) Notice: Subject to any disclaimer, the term of this patent is extended or adjusted under 35 U.S.C. 154(b) by 0 days.

(21) Appl. No.: 09/287,617

(22) Filed: Apr. 7, 1999

(51) Int. Cl.$^7$ ........................................................ A61B 5/05
(52) U.S. Cl. ............................. 600/350; 128/903; 600/343; 600/361
(58) Field of Search ............................... 600/350, 309, 600/322, 348, 347, 343, 361, 365, 315, 549, 302; 128/903

(56) References Cited

U.S. PATENT DOCUMENTS 3,340,866 * 9/1967 Noller ................................. 600/302
3,480,003 11/1969 Crites .

(List continued on next page.)

FOREIGN PATENT DOCUMENTS

WO 98/02209 1/1998 (WO) .

OTHER PUBLICATIONS

An endoscopically deliverable tissue–transfixing device for securing biosensors in the gastrointestinal tract; C. Paul Swain et al., Gastrointestinal Endoscopy, vol. 40, No. 6, 1994.
Keeping an Eye on the Baby, NASA Tech Briefs, Feb. 1999, www.nasatech.com.
Miniaturized Transmitter to be Used in Efforts to Save Babies, NASA Ames Research Center, John Bluck, Nov. 18, 1998 e–mail, Release 98–65AR.
Ambulatory Reflux Testing, Medtronics Sysectics, Medtronics, Inc., Mar. 9, 1999, Web page.
Digitrapper™ MkIII Ambulatory pH Recorder; Medtronic Brochure, 1998.
Manometric Catheters, Zinetics Medical, Inc. Brochure.
Zinetics® Medical, Inc., Critical Care pH Systems, Zinetics Medical, Inc. Brochure, ZMAC rev. 3.
Zinetics 24M, Ambulatory pH Catheters, Zinetics Medical, Inc., ZM24M rev/01.
Pill–Shaped Implantable Biotelemeters, Nasa, Sensors 2000!, Ames Research Center, http://s2k.arc.nasa.gov/.
8.2 24–h pH–metry, *Clinical Procedures in Children*, pp. 143–151.
Implantable Biotelemetry System for Preterm Labor and Fetal Monitoring, National Aeronautics and Space Administration, Ames Research Center.
An ambulant porcine model of acid reflux used to evaluate endoscopic gastroplasty, S.S. Kadirkamanathan et al., *Gastrointestinal Science Research Unit*, The London Hospital, pp. 782–788, 1999.
*Endoscopic Ligator, Information for Use*, C.R. Bard, Inc., Issued Jul. 1998.

* cited by examiner

Primary Examiner—Eric F. Winakur
(74) Attorney, Agent, or Firm—Knobbe, Martens, Olson & Bear, LLP

(57) ABSTRACT

Disclosed is an ambulatory system for detecting, recording, and analyzing gastroesophageal reflux or intraesophageal pressure. The system includes an implantable sensor and radiofrequency transmitter, an external receiver and recorder, and an analysis software package. This system provides for monitoring any of various physiological parameters, including pH, temperature, and pressure, within the esophagus or other body lumens.

37 Claims, 4 Drawing Sheets

U.S. PATENT DOCUMENTS

| | | | |
|---|---|---|---|
| 4,257,420 | 3/1981 | Terayama . | |
| 4,326,535 | 4/1982 | Steffel et al. . | |
| 4,503,859 | 3/1985 | Petty et al. . | |
| 4,546,436 | 10/1985 | Schneider et al. . | |
| 4,561,450 | 12/1985 | Bryant . | |
| 4,618,929 | 10/1986 | Miller et al. . | |
| 4,748,562 | 5/1988 | Miller et al. . | |
| 4,823,808 | * 4/1989 | Clegg et al. | 600/586 |
| 4,924,877 | 5/1990 | Brooks . | |
| 4,967,759 | 11/1990 | Teves . | |
| 4,981,470 | * 1/1991 | Bombeck, IV | 600/350 |
| 4,991,590 | 2/1991 | Shi . | |
| 5,018,529 | 5/1991 | Tenerz et al. . | |
| 5,117,827 | * 6/1992 | Stuebe et al. | 600/350 |
| 5,127,404 | 7/1992 | Wyborny et al. . | |
| 5,153,584 | 10/1992 | Engira . | |
| 5,247,938 | * 9/1993 | Silverstein et al. | 600/459 |
| 5,269,789 | 12/1993 | Chin et al. . | |
| 5,297,437 | 3/1994 | Schneider . | |
| 5,301,673 | 4/1994 | Rabito et al. . | |
| 5,368,027 | * 11/1994 | Lubbers et al. | 600/345 |
| 5,381,800 | 1/1995 | Angelchik . | |
| 5,398,844 | 3/1995 | Zaslavsky et al. . | |
| 5,479,935 | 1/1996 | Essen-Moller . | |
| 5,624,453 | 4/1997 | Ahmed . | |
| 5,833,625 | 11/1998 | Essen-Moller . | |
| 5,836,895 | 11/1998 | Ramsey, III . | |
| 5,984,875 | * 11/1999 | Brune | 600/549 |

REMOTE PHYSIOLOGICAL MONITORING SYSTEM

BACKGROUND OF THE INVENTION

1. Field of the Invention

The present invention relates to minimally invasive physiological monitoring systems. More particularly, the present invention monitors one or more parameters in the esophagus, such as pH, in connection with the detection of gastroesophageal reflux disease.

2. Background of the Invention

Gastroesophageal reflux is a condition in which gastric acid refluxes, or flows in the direction opposite to the normal flow, from the stomach into the esophagus. Frequent reflux episodes may result in a potentially severe problem known as gastroesophageal reflux disease (GERD). GERD is the most common cause of dyspepsia or heartburn. GERD affects approximately 75 million adults in the United States on at least an intermittent basis, and approximately 13 million adults on a daily basis. As a common cause of chest pain, GERD frequently mimics the symptoms of a myocardial infarction or severe angina pectoris, which are signs of severe coronary artery disease. Because their treatments and outcomes are different, distinguishing between GERD and coronary artery disease is of paramount diagnostic importance to the patient and physician.

The lower esophageal sphincter (LES), or valve, is composed of a smooth muscle ring located at the gastroesophageal junction, and it plays a key role in the pathogenesis of GERD. Factors that cause or contribute to GERD include the following: transient relaxation of the LES, delayed stomach emptying, and ineffective esophageal clearance. Another cause of GERD is decreased resting tone of the LES, which produces incompetence (incomplete closing) of the LES.

At rest, the LES maintains a high pressure, between 10 and 30 mm Hg above intragastric pressure. Upon deglutition (swallowing), the LES relaxes before the esophagus contracts, allowing food to pass through into the stomach. After food passes into the stomach, the LES contracts to prevent the stomach contents, including gastric acid, from refluxing into the esophagus. The mechanism of the LES contraction and relaxation is influenced by vagus nerve innervation and hormonal control by gastrin and possibly other gastrointestinal hormones.

Complications of GERD include esophageal erosion, esophageal ulcer, and esophageal stricture. Stricture formation results from scarring of the esophagus following prolonged exposure of the esophageal mucosa to acid reflux. The most common clinical manifestation of stricture is dysphagia (difficulty swallowing). Unlike dysphagia from nonstrictured esophageal reflux, dysphagia caused by stricture is a progressive disorder in that the size of a bolus which can pass into the stomach becomes progressively smaller. Prolonged exposure of esophageal mucosa to acid often leads to a precancerous condition known as Barrett's esophagus. Barrett's esophagus is characterized by the replacement of the normal squamous epithelium that lines the esophagus with abnormal columnar epithelium. Barrett's esophagus is clinically important not only as a marker of severe reflux, but also as a precursor to esophageal cancer.

Efforts have been made to define and report as reflux rapid changes of intraesophageal pH, even while the pH remains within the normal esophageal pH range of 4 to 7. Such pH changes, however, can be difficult to prove to be caused by true gastroesophageal reflux, and in some instances may not be caused by reflux.

Some have measured gastroesophageal reflux with radioisotope techniques. With these techniques, a radiolabeled meal is fed to the patient. With a gamma camera positioned externally on the patient's chest or internally within the esophagus, it is possible to detect gastroesophageal reflux containing the isotope, regardless of pH. The use of radioactive material and the expense of stationary or ambulatory gamma cameras make the radioisotope method for detection of reflux unattractive.

Intestinal impedance has previously been used as a surrogate for measurement of gastric emptying into the intestines. In such studies, a liquid or solid meal is administered to a patient, and changes in intestinal impedance are monitored from external electrodes around the abdomen.

The primary and most reliable method of objectively diagnosing GERD, however, is 24-hour measurement of pH within the lower esophagus. The normal pH range in the esophagus is between 4 and 7. As a general rule, when gastric acid enters the esophagus from the stomach, the intraesophageal pH drops below 4. An epoch of one second or more during which the intraesophageal pH falls below 4 is considered a reflux event.

Certain methods and apparatus are known in the prior art for 24-hour monitoring of intraesophageal pH in patients with suspected GERD. An example of a system for ambulatory 24-hour recording of gastroesophageal reflux is the Digitrapper™ System (manufactured by Synectics Medical AB, in Stockholm, Sweden) used with glass or Monocrystant™ pH catheters (as described in U.S. Pat. No. 4,119,498) and with the analysis software EsopHogram™ (by Gastrosoft, Inc. in Dallas, Tex.). These prior art systems typically measure pH in the esophageal tract with an intraesophageal catheter and generate reports regarding esophageal exposure of gastric juice.

Currently, ambulatory esophageal pH monitoring is performed by passing a pH catheter transnasally into the esophagus, to a point approximately 5 cm above the LES. The proximal end of the nasoesophageal catheter extends outside the patient's nose and is usually taped down to the cheek in two places and draped over the ear.

The use of this indwelling nasoesophageal catheter for ambulatory pH monitoring presents a number of disadvantages. Almost invariably, the catheter's presence is very uncomfortable to patients, who frequently develop a sore throat and rhinorrhea (runny nose) because of local irritation of oropharyngeal and nasopharyngeal mucous membranes, respectively, from the catheter. In addition, many patients are embarrassed to be seen in public with the catheter assembly attached to their faces. Furthermore, patients frequently experience an increased swallowing frequency when the catheter is in place, due to reflex stimulation. This increased swallowing introduces a significant amount of air into the stomach, which can cause abdominal discomfort. Finally, increased swallowing in response to the catheter's presence may erroneously raise a patient's intraesophageal pH readings because saliva is alkaline.

Thus, there remains a need for an ambulatory system that avoids the use of an indwelling nasoesophageal catheter during the assessment of esophageal pH to detect gastroesophageal reflux.

In addition, such a system that avoids the use of an indwelling nasoesophageal catheter is also needed for ambulatory esophageal manometry, i.e., the assessment of intraesophageal pressure. Esophageal manometry is a procedure used to diagnose abnormal esophageal motility and abnormal LES pressure, features that are hallmarks of certain esophageal diseases such as achalasia.

SUMMARY OF THE INVENTION

There is provided in accordance with one aspect of the present invention a method and apparatus for remotely monitoring a physiological parameter in a body lumen of a person. The method comprises the steps of temporarily attaching a monitor to a wall of the body lumen, and recording the physiological data. The monitor comprises a transducer of one or more physiological parameters and, in some embodiments, a power source. In one aspect of the present invention, the body lumen is the human esophagus.

In accordance with another aspect of the present invention, the monitor further comprises a radiofrequency transmitter, and the physiological data that is transduced by the monitor is transmitted to a radiofrequency receiver and a recording device located outside of the person's body.

In accordance with other aspects of the present invention, the monitor also comprises a microprocessor and/or a digital recorder that records the physiological data. The physiological data can be transferred from the digital recorder or microprocessor within the monitor to an external data retrieval device, such as a magnetic field reader or a radiofrequency receiver.

The physiological parameters that are transduced and transmitted by the present invention can include pH, pressure, temperature, ion or other solute concentration, or other physiological parameters.

In accordance with some aspects of the present invention, there is provided a computer software program which analyzes the physiological parameter data that is obtained over a period of time by the monitor.

In accordance with other aspects of the present invention, there is provided a method for attaching a physiological parameter monitor to the wall of a body lumen, such as the esophagus. The attachment can occur by means of an adhesive substance. The attachment method can alternatively comprise a device that expands or widens to span the diameter of the body lumen, so as to attach the monitor to the lumen wall at two or more contact points. As a further aspect of the invention, the monitor can be attached to the body lumen by means of suturing or stapling, or using tacks, pins, elastic bands, or other attachment structures that at least partially capture or penetrate the mucosa of the lumen wall.

Further features and advantages of the present invention will become apparent from the detailed description of preferred embodiments which follows, when considered together with the attached drawings and claims.

DETAILED DESCRIPTION OF THE PREFERRED EMBODIMENT

The present invention provides a method and system for monitoring physiological parameters within a body lumen (cavity). The invention also comprises methods for attaching a physiological parameter monitor to a wall of a body lumen. The term "lumen" as used herein refers to the space within a tubular wall (e.g., a vessel) or the cavity within a hollow organ. While the invention is described in detail as applied to the human esophagus, those skilled in the art will appreciate that it can apply to other body lumens or cavities, such as those of the stomach, colon, rectum, bladder, uterus, vagina, biliary ducts (including the common bile duct), or blood vessels. The term "esophagus" in this discussion includes the lower esophageal sphincter (LES). Where different embodiments have like elements, like reference numbers are used.

Figure 1:
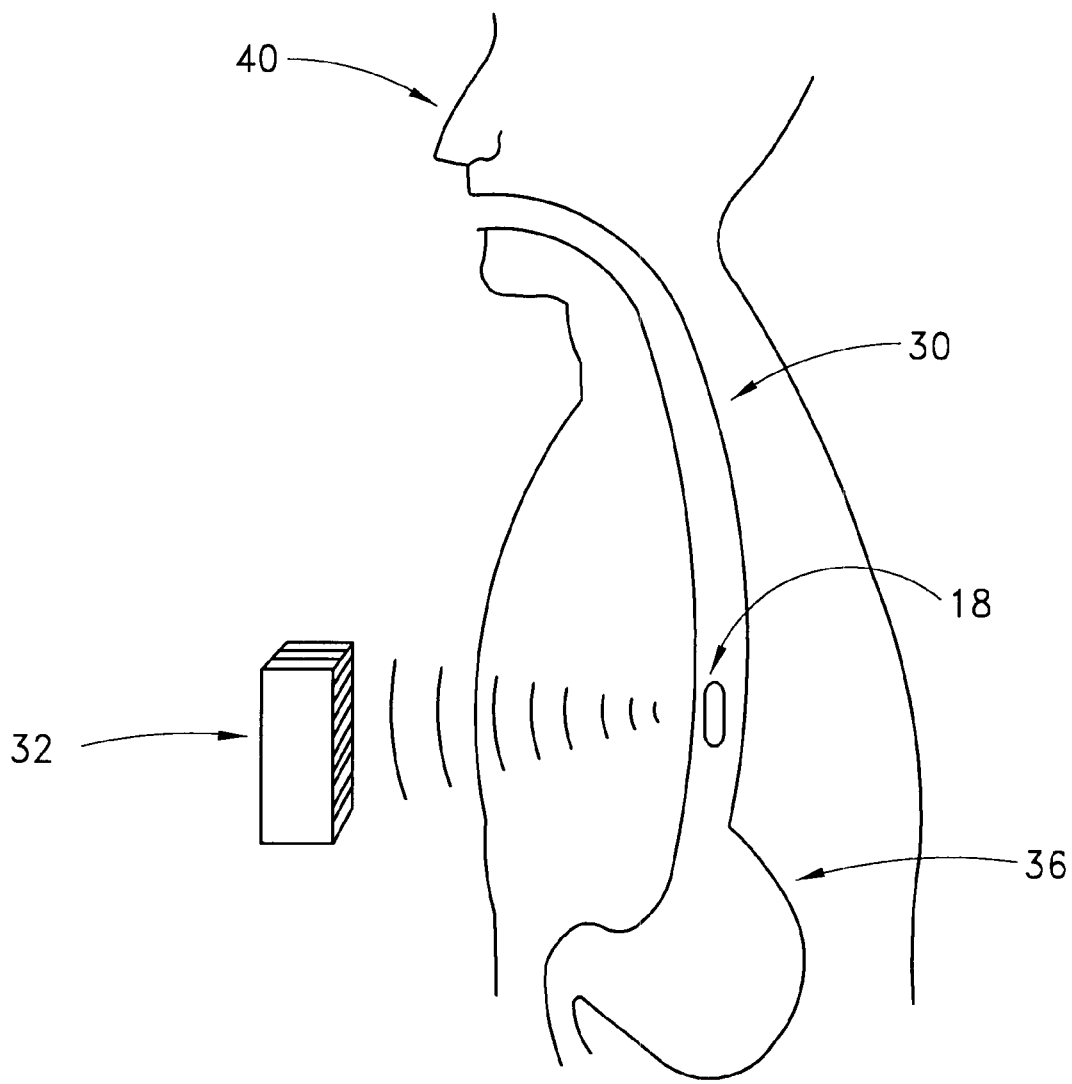
FIG. 1 is a schematic side view of a person with the physiological parameter monitor in place within the esophagus.

FIG. 1 illustrates how physiological parameter data can be relayed by the monitor 18, which is positioned within the esophagus 30, to a radiofrequency receiver 32 (hereinafter "radioreceiver") located outside the body of a person 40.

In certain embodiments, this transmission of data is accomplished via telemetry in real time. The radioreceiver 32 receives physiological parameter data almost immediately after it is transmitted from the monitor 18. After reception of this data, the radioreceiver 32 apparatus can record, manipulate, interpret and/or display the data, using technology well known to those skilled in the art. In certain embodiments, the patient can wear the receiver 32 and recorder on, for example, a belt, bracelet, arm or leg band, or necklace during the period of pH study or other analysis.

The receiver 32 and recording apparatus can have buttons or other switches thereon that enable the patient or other person to mark certain events in time during the recording period, such as when symptoms occur, when the patient is eating, when the patient is recumbent (either supine or prone), or when the patient is about to sleep. This event marking can be made in any recording medium that is used for recording the physiological parameter, such as magnetic tape or an electronic digital memory chip, in ways that are well known to those of skill in the art.

The monitor 18 can be made to sense the position of the patient, whether horizontal, vertical, or somewhere between horizontal and vertical. Such position sensing can be accomplished through the use of electrical switches that utilize floating fluid bubbles, as used in mechanical level sensing, or electronic gyroscopic techniques as are known to those skilled in the art.

In certain embodiments, the monitor 18 can record and compress physiological parameter data as it is received, rather than transmit the data in real time. Following the assessment period, or at intervals therein, an external receiver can be used to download pulses of condensed data. Transmission of data can be initiated at predetermined intervals or by an activation signal sent from the external receiver or other activating device to the monitor 18, as will be understood by those of skill in the art. In this manner, a tabletop receiver can be utilized, either at the patient's home, or in the physician's office or other clinical site.

In other embodiments, the monitor 18 can record, compress, and store physiological parameter data as it is received, using a memory chip or microprocessor 116. The person 40 can excrete the monitor 18 in his or her stool, and the monitor 18 can be retrieved. Subsequently, data stored in the monitor 18 can be downloaded into an external data retrieval device, which can be a computer or other analysis machine located outside the patient's body. This downloading can be in response to an activation signal, using magnetic field or radiofrequency technology well known to those skilled in the art.

Although the typical gastroesophageal reflux study lasts 24 hours, other time periods for this study can exist, such as 48 hours or longer. Through the use of this invention, it is possible that fewer than 24 hours may be needed to establish the diagnosis of GERD, particularly because real-time monitoring can provide nearly immediate evidence of reflux events. The actual durations of various reflux studies using the present invention will be apparent to those of skill in the art.

Figure 2:
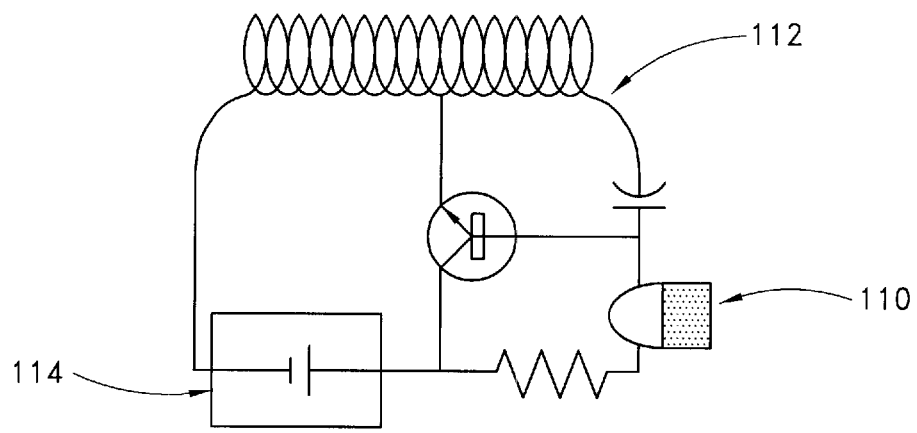
FIG. 2 is a schematic view of one embodiment of an electrical circuit for the physiological parameter monitor.

FIG. 2 illustrates a simplified circuit for a monitor of a physiological parameter (hereinafter "monitor"). This monitor may also be referred to as a "probe" or "pill" by those skilled in the art. In the particular embodiment illustrated in FIG. 2, pH is the physiological parameter to be sensed, and it is detected by a transducer 110, which comprises a pH sensor and preferably also a reference sensor. In the present invention, a monitoring transducer (hereinafter "transducer") can be any transducer that senses a physiological parameter and furnishes a signal one of whose electrical characteristics, such as current or voltage, is proportional to the measured physiological parameter.

Although a pH sensor is described here, those skilled in the art will appreciate that a sensor of any of a variety of other physiological parameters, such as pressure or temperature, can be detected and monitored. Sometimes, temperature and/or pressure will be sensed and transduced together with pH, in order to adjust the pH readings and make them more accurate, or to supply additional data helpful in the analysis of the patient's condition. In addition, the concentration of ions or other solutes present in body fluids can be detected and analyzed using this invention. For example, ions such as sodium, potassium, calcium, magnesium, chloride, bicarbonate, or phosphate may be measured. Other solutes whose concentrations in body fluids are of importance and may be measured by the present invention include, among others, glucose, bilirubin (total, conjugated, or unconjugated), creatinine, blood urea nitrogen, urinary nitrogen, renin, and angiotensin. Any combination of two or more of the preceding parameters may be sensed by the transducer 110. For any physiological parameter sensed and transduced by means of a transducer, a reference sensor may or may not be required.

FIG. 2 also illustrates a radiofrequency transmitter 112 and a power source 114. The radiofrequency transmitter 112 can comprise an antenna (or antenna coil), and the antenna can be at least in part external to the monitor shell 120 (seen in FIG. 4). Alternatively, the antenna, if present, can be entirely self-contained within the monitor shell 120. The monitor can be sealed to protect against seepage of fluids from the body into the monitor's internal compartment(s). When located within the monitor 18, the power source 114 can be a battery or capacitor or any other device that is capable of storing an electrical charge at least temporarily.

In alternative embodiments, the source of power to the monitor 18 can be external to the monitor 18 itself. For example, the monitor can derive power from an external electromagnetic radiofrequency (RF) source, as occurs with passive RF telemetry techniques, such as RF coupling, that are well known to those skilled in the art. The monitor 18 can be energized by a time-varying RF wave that is transmitted by an external source 32, also known as an "interrogator," which can also serve as a reader of data from the monitor 18. When the RF field passes through an antenna coil located within the monitor 18, there is an AC voltage generated across the coil. This voltage is rectified to supply power to the monitor 18. The physiological parameter data stored in the monitor 18 is transmitted back to the interrogator 32 (FIG. 1), in a process often referred to as "backscattering." By detecting the backscattering signal, the data stored in the monitor 18 can be fully identified.

Other sources of power for the monitor 18 include light, body heat, and the potential difference in voltage that can be generated in body fluids and detected by electrodes made of varying materials. The harnessing of such power sources for biotelemetry purposes is well described in R. Stuart Mackay: *Bio-Medical Telemetry, Sensing and Transmitting Biological Information from Animals and Man*, 2d ed., IEEE Press, New York, 1993, whose section entitled "Electronics: Power Sources" is hereby incorporated herein by reference.

Figure 3:
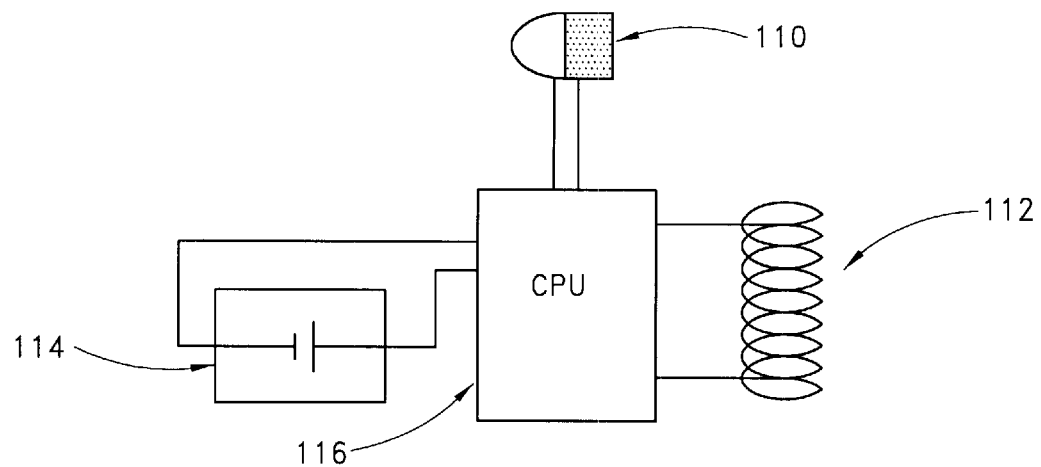
FIG. 3 is a schematic view of another embodiment of an electrical circuit for the physiological parameter monitor, which circuit also includes a microprocessor.

FIG. 3 illustrates alternative embodiments of the physiological parameter monitor circuitry. In this embodiment, a microprocessor 116, also called a central processing unit (CPU), is illustrated. This microprocessor 116 can perform one or more functions, including temporary storage or memory of data, reception of input signal from the transducer, and transformation of analog data to digital output, among other functions that will be apparent to those skilled in the art. The transducer 110, radiofrequency transmitter 112, and power supply 114 are also present. Many other circuitry components that can help to generate, amplify, modify, or clarify the electrical signal can be used in other embodiments of the monitor. Such components include buffers, amplifiers, signal offset controls, signal gain controls, low pass filters, output voltage clamps, and analog-to-digital converters, among others. Numerous possible circuitry features of a portable pH monitoring device, all of which can be used in the present invention, are well described in U.S. Pat. No. 4,748,562 by Miller, et al., the disclosure of which is incorporated in its entirety herein by reference.

In certain embodiments, the monitor 18 further comprises a digital recorder or memory chip (not illustrated), which records the transduced physiological parameter data. This recorder or memory chip will allow temporary storage of this data accumulated over time (e.g., over a period of 24 hours for a typical gastroesophageal reflux study).

Figure 4:
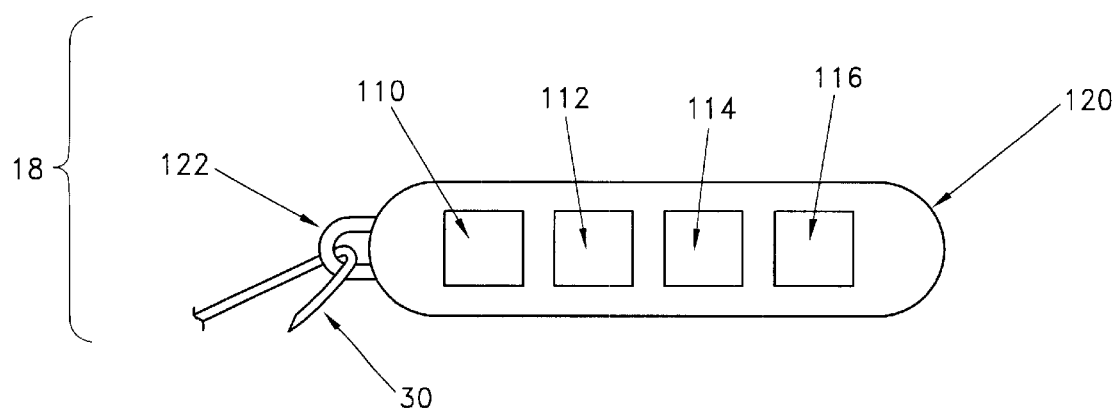
FIG. 4 is a schematic side view of on embodiment of a physiological parameter monitor.

FIG. 4 schematically illustrates the configuration of certain embodiments of the physiological monitor 18. In this embodiment, an outer shell 120 surrounds the monitor's electronic components. The transducer 110, the radiofrequency transmitter 112, the power supply 114, and a microprocessor 116 are encased within the outer shell 120. In certain embodiments, the shape of the shell 120 can resemble that of a pill or gel capsule, as commonly used in various oral drug delivery systems.

The shell 120 can be made of any of various materials, including plastics such as polyethylene, polytetrafluoroethelyne (Teflon®), nylon, delrin, or polyethylene terephthalate. The material used for the shell 120 should be resistant to water and acidic environments because the shell will be exposed, in some embodiments, to food, water, and gastrointestinal contents, including gastric acid, which is very caustic (with a pH of approximately 1).

The shell 120 can have a lubricious coating applied to its outer surface, which reduces friction between the shell 120 and any object or material that comes in contact with the shell 120, such as the esophageal wall or any food or fluids that flow down the esophagus 30 past the monitor. Such a coating can be made of silicone, silicone derivatives, or other hydrophilic materials that will be apparent to those skilled in the art. This slippery coating on the surface of the shell 120 will reduce the likelihood of occurrence of the following events: (1) ingested material will adhere to the monitor 18, (2) the esophagus 30 will become irritated from repeated contact with the monitor 18 during peristalsis of the esophagus 30, and (3) peristalsis or flowing food or fluid will cause detachment of the monitor 18 from its attachment site.

In certain embodiments, the shape of the shell 120 is streamlined and smooth and does not have sharp edges. This feature helps to avoid injury to the gastrointestinal mucosa during the following time periods: (1) during endoscopic placement of the monitor 18, (2) while the monitor 18 is attached to the esophagus, and, (3) if and when the monitor 18 becomes unattached from the esophageal wall, while the monitor 18 passes through the gastrointestinal tract and is excreted in the stool.

The physiological monitor 18 can be placed in the esophagus 30 in a variety of ways. In certain embodiments of the present method, the monitor 18 is placed into the esophagus 30 through the use of a flexible or rigid endoscope 160 inserted through the nose or mouth of the person 40. The monitor 18 can be constrained within or by a deployment device, such as a catheter, until attachment is visually verified through the endoscope 160 by the physician. Then the monitor 18 can be intentionally deployed and left within the esophagus, using methods known to those of skill in the art.

In other embodiments, a surgeon can attach the monitor 18 directly to the inner aspect of the esophageal wall through an opening in the esophagus 30 (esophagotomy) or stomach 36 (gastrotomy).

The physiological monitor 18 can be attached to the esophagus 30 in a variety of ways, also referred to herein as "attachment means." In certain embodiments, as shown in FIG. 4, the monitor shell 120 has an eyelet attachment 122, which serves to hold a suture 30, string, staple, or other securing structure, which can secure the monitor to the wall of the esophagus or other body lumen wall. Besides the eyelet attachment 122, many other possible modifications of or attachments to the shell 120, such as one or more loops, rings, brackets, tacks, hooks, strings, threads, or screws, can be utilized to facilitate the attachment or fixation of the monitor to a lumenal wall.

The monitor 18 can, in some embodiments, be attached to the esophagus 30 through the use of a clip, which may resemble, for example, an alligator clip. This clip may or may not utilize a spring mechanism, and it can hold the monitor in place by capturing, or "pinching," the mucosa and submucosa of the esophagus 30 between its arms or "jaws." The clip can have one or more of its parts made of one or more absorbable or dissolvable materials, such as are described below and are known to those skilled in the art. This dissolvable material can facilitate the removal of the monitor 18 from the wall of the esophagus 30 after a given period of time. As materials in the clip dissolve, the tension in the clip that causes it to hold onto, or pinch, the esophagus 30 will eventually decrease, and the clip will break free of the esophagus 30 and travel through the gastrointestinal tract and into the patient's stool.

Figure 5:
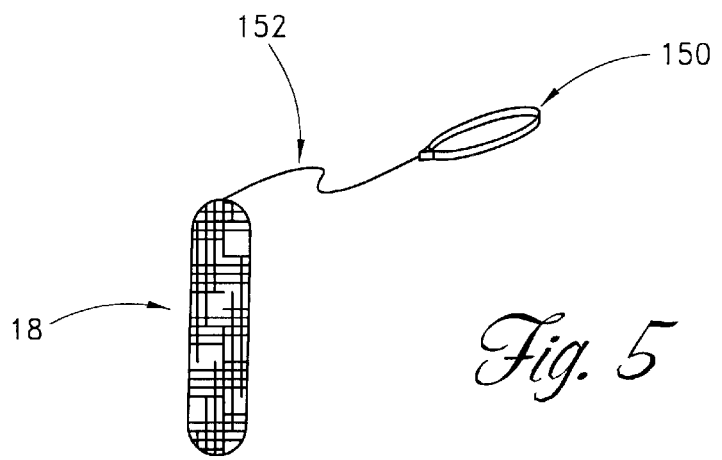
FIG. 5 is a schematic side view of the physiological parameter monitor with an elastic band attached.

In certain embodiments of the present method, as shown in FIG. 5, the monitor 18 is attached to the esophagus 30 by means of a suture loop or an elastic band 150. The elastic band can be attached to the monitor 18 with an absorbable or nonabsorbable suture, string, or thread, otherwise referred to as a "tether" 152. This tether 152 can be made from a variety of materials, such as a polymeric filament, which can be absorbable or nonabsorbable in vivo.

In some embodiments, the tether 152 can be attached to a tooth, such as a molar, of a person. The monitor 18 is thus suspended in the esophagus by the tether 152, which is attached at its other end to the tooth. The attachment to the tooth can be performed by means of an elastic band, plastic band, adhesive materials, or any other means for attaching a structure to a tooth, as are well known in the dental art.

Figure 6:
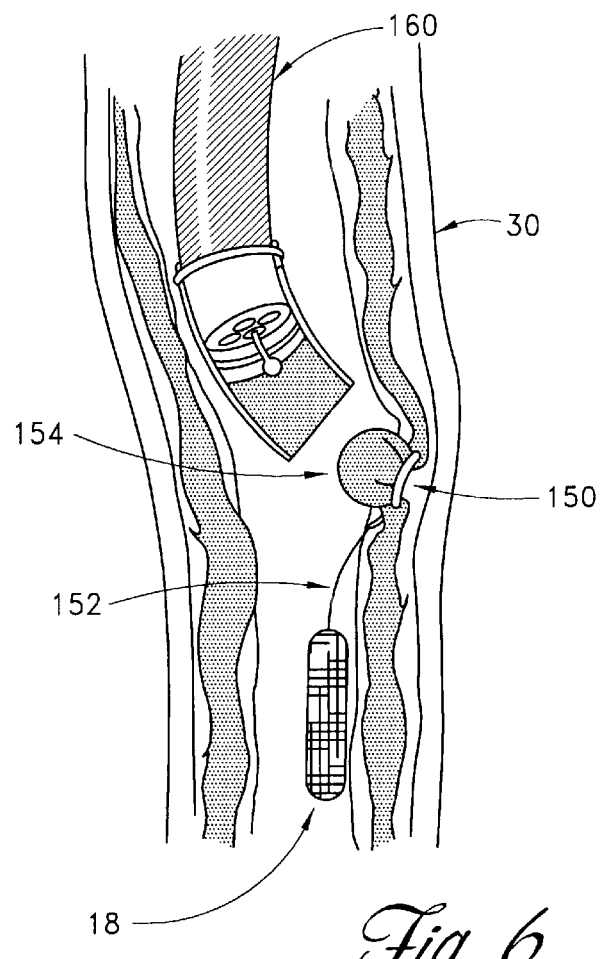
FIG. 6 is a cut-away side view of the esophagus with endoscopic placement of the monitor by means of an elastic band

As shown in FIG. 6, the elastic band 150 can be placed around a protuberance 154 in the wall of the esophagus 30 or other body lumen. Such a protuberance 154 can be found as a naturally occurring pathological structure, such as a polyp, or it can be formed by a physician (as a "quasi-polyp") using an endoscope 160 by applying suction to the wall of the esophagus 30. Such suction-induced protuberances 154 in the esophagus 30 are well known to those skilled in the art and represent a commonly used method of ligating (tying off) esophageal varices, which are enlarged blood vessels in the wall of the esophagus 30 caused by elevated portal venous pressure.

Although endoscopic ligation techniques typically result in necrosis of the tissue that is elevated into a protuberance 154 and ligated, in the present method the aim of this technique is merely to provide a structure in the lumen of the esophagus 30 or other body lumen upon which to attach temporarily the physiological parameter monitor 18. Thus, it may be desirable not to attach the elastic band 150 to the protuberance 154 too tightly, so as to avoid compromise to the blood supply to the protuberance 154.

In order to avoid exposure of the attachment site to refluxed gastric acid, it will at times be desirable to attach the monitor 18 to the esophagus 30 at a site some significant distance rostral (cephalad) to the LES. The monitor 18 can thereby be suspended from the esophageal attachment site by the tether 152, such that the monitor 18 is positioned close (typically 5 cm superior) to the LES, to facilitate detection of gastroesophageal reflux. This technique optimizes the likelihood that while the monitor 18 is exposed to refluxed gastric acid, the esophageal attachment site is not so exposed because it is sufficiently far from the LES as to avoid the surge of refluxed gastric contents. Distances between the attachment site and the monitor 18 of at least about 0.5 cm, and as much as 10 cm or more, may be utilized for this purpose.

In other embodiments of the present method, the monitor 18 can be attached to the wall of the esophagus 30 or other body lumen using an adhesive substance (hereinafter "adhesive") either alone or in combination with the mechanical attachment structures disclosed herein. This adhesive can be any of a variety of cyanoacrylates, derivatives of cyanoacrylates, or any other adhesive compound with acceptable toxicity to human esophageal cells that provides the necessary adhesion properties required to secure the monitor 18 to the wall of the esophagus 30 for at least a sufficient monitoring period of time. In certain embodiments the monitor 18 can be directly attached to the wall of the esophagus 30 with the adhesive. In other embodiments, the monitor 18 can be attached indirectly, utilizing an intermediate structure, such as an anchor, to which the monitor 18 attaches and which is in turn adhered to the esophagus 30 by means of the adhesive. One example of this type of intermediate structure is an elongate strip of cloth or plastic, secured at one end to the shell 120 and having a tissue attachment surface along its length or at the other end for enhancing adhesive or mechanical bonding to the esophagus 30. Other intermediate structures and materials can be used, as will be apparent to those skilled in the art.

In other embodiments of the present method, the monitor 18 is attached to the esophagus 30 using a self-expandable support structure (not illustrated) that expands or widens to span the diameter of the body lumen, so as to retain the monitor 18 therein. Suitable support structures include self-expandable wire cages, such as are used for supporting grafts in the abdominal aorta and elsewhere in the vascular system. Stents, struts, and other structural devices known to those of skill in the art may be used. Many of these structural devices are used in the fields of vascular radiology and cardiology for the purpose of maintaining patency in blood vessels. These support structures can be made from a variety of materials such as stainless steel, nitinol, or polymeric filament, which can be absorbable or nonabsorbable in vivo.

In further embodiments of the present method, the monitor 18 is attached to the esophagus 30 using one or more sutures, clips, staples, tacks, pins, hooks, barbs, or other securing structures that can at least partially penetrate the mucosa of the esophagus. These securing structures can be made from a variety of materials, including absorbable materials, such as polylactic acid (PLA) or copolymers of PLA and glycolic acid, or polymers of p-dioxanone and 1,4-dioxepan-2-one. A variety of absorbable polyesters of hydroxycarboxylic acids may be used, such as polylactide, polyglycolide, and copolymers of lactide and glycolide, as described in U.S. Pat. Nos. 3,636,956 and 3,297,033, which are hereby incorporated in their entirety herein by reference. The use of absorbable materials allows the securing structure to dissolve or resorb into human tissue after a known or establishable time range, such as 48 to 72 hours, and the monitor 18 can thereby become detached from the esophagus 30 and can then be excreted in the patient's stool.

For example, one or more short pointed barbs can be integrally formed with the shell 120 or secured thereto using any of a variety of attachment techniques which are suitable depending upon the composition of the shell 120 and the barb. This embodiment can be pressed into the wall of the esophagus, thereby causing the barb or barbs to penetrate the mucosa and enter the submucosa. Preferably, any such barbs will not penetrate the muscular wall surrounding the submucosa. Hooks may also be attached to or integrally formed with the shell 120, so that the shell 120 can be hooked onto the wall of the esophagus, possibly in combination with the use of a bioadhesive. Such hooks and barbs may be formed from a bioabsorbable or dissolvable material as has been discussed, to permit detachment of the monitor after a suitable period of time.

Alternatively, the monitor 18 may be secured to the wall of the esophagus or other tissue surface by one or more bands which wrap around the monitor 18 and are attached at either end to the tissue surface. Either end of the band may be attached to the tissue surface such as through the use of barbs or hooks, as discussed above. As a further alternative, the monitor 18 may be secured to the tissue surface using a bioabsorbable suture as are known in the art. The suture may be passed through the mucosa, travel laterally through the submucosa and exit the mucosa to form an attachment loop. The suture may travel over the monitor 18 and again travel through the mucosa, along the submucosa and exit the mucosa where it is tied off with the other suture end. This may be accomplished using any of a variety of endoscopic instruments adapted for suturing as will be apparent to those of skill in the art.

Because these latter methods are invasive and cause disruption of the esophageal mucosa and possibly the esophageal musculature, they may produce complications such as scarring, stricture, perforation, or bleeding of the esophagus. This same concept applies to other body lumens as well. The desirability of any particular attachment structure will be apparent in the clinical judgment of physicians, taking into account the parameter(s) to be measured and the particular patient's needs and circumstances.

In some embodiments, a computer software program is used to analyze the physiological parameter data obtained over a period of time. Such analysis can include graphical representation of the data, identification of abnormal values outside the range of normal (such as pH values outside the range of about 4 to 7, which may represent reflux events), and averaging of data values, among other types of analysis that will be apparent to those skilled in the art.

Although the present invention has been described in terms of certain preferred embodiments, other embodiments of the invention will become apparent to those of skill in the art in view of the disclosure herein. Accordingly, the scope of the present invention is not intended to be limited by the foregoing, but rather by reference to the attached claims.

What is claimed is:

1. A method of remotely monitoring a physiological parameter in a body lumen of a person, comprising the steps of:

providing a monitor comprising a transducer of a physiological parameter and an attachment band;

attaching the band to a tissue protuberance on a wall of the lumen;

exposing said monitor to an environment in which to assess the physiological parameter and obtain physiological parameter data;

recording said physiological parameter data;

digitizing said physiological parameter data to form digitized data; and transmitting said digitized data as a radiofrequency signal from said monitor to a receiver.

2. A method as in claim 1, wherein said body lumen is an esophagus.

3. A method as in claim 1, wherein said monitor further comprises a radiofrequency transmitter, and said receiver is located outside said person's body.

4. A method as in claim 1 wherein said monitor further comprises a microprocessor.

5. A method as in claim 1, wherein said monitor further comprises a digital recorder that records said physiological parameter data.

6. A method as in claim 5, further comprising the step of transferring said physiological parameter data from said digital recorder to an external data retrieval device.

7. A method as in claim 1, wherein said physiological parameter is selected from the group consisting of pH, temperature, and pressure.

8. A method as in claim 7, wherein said physiological parameter data comprises data concerning at least two of said parameters.

9. A method as in claim 7, wherein said physiological parameter data comprises data concerning all three of said parameters.

10. A method as in claim 1, wherein said physiological parameter comprises the concentration of ions within a body fluid.

11. A method as in claim 10, wherein said ions are selected from the group consisting of sodium, potassium, calcium, magnesium, chloride, bicarbonate, and phosphate.

12. A method as in claim 1, wherein said physiological parameter comprises the concentration of a solute within a body fluid.

13. A method as in claim 12, wherein said solute is selected from the group consisting of glucose, bilirubin, creatinine, blood urea nitrogen, urinary nitrogen, renin, and angiotensin.

14. A method as in claim 1, further comprising the step of using a computer and a computer program to analyze said physiological parameter data obtained over a period of time.

15. A method as in claim 1, further comprising the step of forming the protuberance by applying suction to the wall of the lumen.

16. A method as in claim 1, wherein the attaching step comprises positioning an elastic band around the protuberance.

17. A method of temporarily attaching a physiological parameter monitor to a wall of a body lumen comprising:
    placing said monitor in close proximity to said wall of said lumen, and
    fixing said monitor to said body lumen wall by endoscopically placing a band attached to the monitor around a suction-induced protuberance in the wall of said body lumen.

18. A method as in claim 17, further comprising the step of forming the protuberance by applying suction to the body lumen wall.

19. A method as in claim 17, wherein the fising step comprises positioning an elastic band around the proturberance.

20. A method of remotely monitoring a physiological parameter in an esophagus of a person, comprising the steps of:
    temporarily attaching a monitor to a suction-induced tissue protuberance in the esophagus, said monitor comprising a transducer of a physiological parameter;
    exposing said monitor to an environment within the lumen of the esophagus in which to assess the physiological parameter and obtain physiological parameter data; and
    recording said physiological parameter data.

21. A method as in claim 20, wherein said physiological parameter is selected from the group consisting of pH, temperature, and pressure.

22. A method as in claim 20, wherein said physiological parameter data comprises data concerning at least two of said parameters.

23. A method as in claim 20, wherein said physiological parameter data comprises data concerning all three of said parameters.

24. A method as in claim 20, further comprising the step of forming the protuberance by applying suction to the wall of the esophagus using an endoscope.

25. A method as in claim 20, further comprising:
    converting said physiological parameter data into a digital signal;
    encoding the digital signal into a radiofrequency signal; and
    transmitting said radiofrequency signal to a radiofrequency receiver.

26. A gastroesophageal reflux monitoring system, comprising:
    an implantable monitor for monitoring at least pH;
    an anchor on the monitor for removably securing the monitor to a suction-induced protuberance on wall of the esophagus; and
    a radiofrequency receiver for positioning outside of the body to receive data from the monitor.

27. A gastroesophageal reflux monitoring system as in claim 26, further comprising an analog-to-digital converter.

28. A method of remotely monitoring a physiological parameter in a body lumen of a person, comprising the steps of:
    providing a monitor comprising a transducer of a physiological parameter and an attachment element;
    attaching the monitor to a wall of the lumen;
    exposing said monitor to an environment in which to assess the physiological parameter and obtain physiological parameter data;
    obtaining said physiological parameter data;
    digitizing said physiological parameter data to form digitized data; and
    transmitting said digitized data as a radiofrequency signal from said monitor to a receiver.

29. A method of remotely monitoring a physiological parameter in a body lumen of a person, comprising the steps of:
    providing a monitor comprising a transducer of a physiological parameter and an attachment element;
    attaching the attachment element to a protuberance in a wall of the lumen;
    exposing said monitor to an environment in which to assess the physiological parameter and obtain physiological parameter data; and
    obtaining said physiological parameter data.

30. A method of temporarily attaching a physiological parameter monitor to a wall of a body lumen comprising:
    placing said monitor in close proximity to said wall of said lumen; and
    fixing said monitor to a protuberance in the wall by a temporary attachment means that is connected to said monitor.

31. A method of temporarily attaching a physiological parameter monitor to a wall of a body lumen comprising:
    placing said monitor in close proximity to said wall of said lumen, and
    fixing said monitor to said wall by attaching the monitor to a suction-induced protuberance in said wall.

32. A method of remotely monitoring a physiological parameter in a body lumen of a person, comprising the steps of:
    providing a monitor comprising a transducer of a physiological parameter and an attachment element;
    attaching the monitor to a wall of the lumen; and
    exposing said monitor to an environment in which to assess the physiological parameter and obtain physiological parameter data; and
    obtaining said physiological parameter data;
    wherein said attaching of said monitor to said wall is accomplished by use of one or more objects selected from the group consisting of tacks, pins, hooks, barbs, clips, and other objects that at least partially penetrate the mucosa of said lumen wall.

33. A method of remotely monitoring a physiological parameter in a body lumen of a person, comprising the steps of:
    providing a monitor comprising a transducer of a physiological parameter and an attachment element;
    attaching the monitor to a wall of the lumen;

exposing said monitor to an environment in which to assess the physiological parameter and obtain physiological parameter data; and obtaining said physiological parameter data;

wherein said attaching of said monitor to the lumen wall is accomplished by use of a clip that pinches the wall of the lumen.

34. A method of remotely monitoring a physiological parameter in a body lumen of a person, comprising the steps of:

providing a monitor comprising a transducer of a physiological parameter and an attachment element;

attaching the monitor to a wall of the lumen;

exposing said monitor to an environment in which to assess the physiological parameter and obtain physiological parameter data; and obtaining said physiological parameter data;

wherein said attaching of said monitor to said wall is accomplished by use of one or more objects selected from the group consisting of tacks, pins, hooks, barbs, clips, and other objects that at least partially penetrate the mucosa of said lumen wall; and wherein said object used for attaching said monitor to the lumen wall is made at least partially of dissolvable materials.

35. A method of remotely monitoring a physiological parameter in a body lumen of a person, comprising the steps of:

providing a monitor comprising a transducer of a physiological parameter and an attachment element;

attaching the monitor to a wall of the lumen;

exposing said monitor to an environment in which to assess the physiological parameter and obtain physiological parameter data; and obtaining said physiological parameter data;

wherein said attaching of said monitor to the lumen wall is accomplished by use of a clip that pinches the wall of the lumen; and wherein said clip used for attaching said monitor to the lumen wall is made at least partially of dissolvable materials.

36. A method of remotely monitoring a physiological parameter in a body lumen of a person, comprising the steps of:

providing a monitor comprising a transducer of a physiological parameter and an attachment element;

attaching the monitor to a wall of the lumen;

exposing said monitor to an environment in which to assess the physiological parameter and obtain physiological parameter data; and obtaining said physiological parameter data;

wherein said attaching of said monitor to said lumen wall is accomplished by use of an elastic band, which is connected to said monitor and which is endoscopically placed around said protuberance on the wall of said lumen.

37. A method of temporarily attaching a physiological parameter monitor to a wall of a body lumen comprising:

placing said monitor in close proximity to said wall of said lumen; and fixing said monitor to said body lumen wall by a temporary attachment means;

wherein said attachment means is an elastic band, which is connected to said monitor and which is endoscopically placed around said protuberance on the wall of said lumen.

* * * * *

UNITED STATES PATENT AND TRADEMARK OFFICE
CERTIFICATE OF CORRECTION

PATENT NO. : 6,285,897 B1
DATED : September 4, 2001
INVENTOR(S) : John T. Kilcoyne et al.

It is certified that error appears in the above-identified patent and that said Letters Patent is hereby corrected as shown below:

<u>Column 11, claim 19,</u>
Line 28, "the fising step" should be -- the fixing step --

<u>Column 14, claim 37,</u>
Line 38, "around said" should be -- around a --

Signed and Sealed this

Twenty-sixth Day of March, 2002

Attest:

JAMES E. ROGAN
*Attesting Officer*    *Director of the United States Patent and Trademark Office*